United States Patent [19]

Mitsunaga et al.

[11] 4,277,488

[45] Jul. 7, 1981

[54] WATER-SOLUBLE BIOTIN-CONTAINING PREPARATION

[75] Inventors: Takayoshi Mitsunaga, Ibaraki; Kiyoto Chinushi, Takatsuki; Tadashi Umezu, Ibaraki, all of Japan

[73] Assignee: Sumitomo Chemical Company, Limited, Osaka, Japan

[21] Appl. No.: 136,564

[22] Filed: Apr. 2, 1980

[51] Int. Cl.³ .................... A61K 31/415; C09K 3/00
[52] U.S. Cl. .......................... 424/273 R; 252/363.5
[58] Field of Search ................. 424/273 R; 252/363.5

[56] References Cited

U.S. PATENT DOCUMENTS

| 2,193,523 | 3/1940 | Schultz | 424/273 R |
| 2,202,307 | 5/1940 | Booher | 424/273 R |

OTHER PUBLICATIONS

C.A. 76: 90066x, 1972.

*Primary Examiner*—Frank Cacciapaglia, Jr.
*Attorney, Agent, or Firm*—Birch, Stewart, Kolasch & Birch

[57] ABSTRACT

A water-soluble biotin-containing preparation prepared by spray-drying an aqueous solution comprising biotin and lactose with ammonia to obtain dried particles. Biotin in this preparation is highly soluble in water.

4 Claims, No Drawings

WATER-SOLUBLE BIOTIN-CONTAINING PREPARATION

The present invention relates to a water-soluble biotin-containing preparation and its production.

As well known, biotin is used as an additive to feed supplements for domestic animals and culture fishes. It is also used as a medicament for prevention and therapy of skin diseases.

Since, however, biotin itself is hardly soluble in water, various inconveniences are encountered on its practical use. For instance, a method for mixing an active ingredient uniformly into feed supplements by dissolving the active ingredient into water and spraying the resultant solution onto the feed supplements is not applicable. Further, for instance, a method for administering an active ingredient orally to domestic animals by dissolving the active ingredient into drinking water or liquid feed supplements and giving the resulting solution to the domestic animals is not applicable. In addition, its absorption rate in domestic animals is small so that the exhibition of its efficiency is low or slow.

In order to overcome the said drawbacks, an extensive study has been made for increasing the solubility of biotin into water. As the result, it has now been found that dried particles containing biotin obtained by spray-drying an aqueous solution comprising biotin and lactose with ammonia is highly soluble in water. This is a finding of unexpected nature, because a mixture of biotin and lactose obtained merely by mechanical blending does not materially contribute in increasing the water-solubility of biotin. It is also notable that dried particles containing biotin obtained by spray-drying an aqueous solution comprising biotin and ammonia without lactose do not show good water-solubility.

The water-soluble biotin-containing preparation of the present invention can be prepared by spray-drying an aqueous solution comprising biotin and lactose with ammonia to obtain dried particles containing biotin.

The aqueous solution to be subjected to spray-drying should contain biotin, lactose and ammonia. The weight proportion of biotin and lactose in the aqueous solution is usually from 1:40 to 1:100. In the aqueous solution, biotin is desired to be completely dissolved. In order to achieve such complete dissolution, the presence of ammonia is needed. The amount of ammonia in the aqueous solution may be such that it is sufficient to dissolve biotin in the aqueous solution. When, for instance, 28% aqueous ammonia is used, it may be usually employed to make a concentration of 0.1% (w/v) or more in the aqueous solution. The resulting aqueous solution has ordinarily a pH of 5 to 9.

As to the procedure for preparation of the aqueous solution, no limitation is present. For instance, the aqueous solution may be prepared by adding lactose to water containing ammonia and then adding biotin thereto. Further, for instance, it may be prepared by adding a mixture of lactose and biotin to water containing ammonia. Furthermore, for instance, it may be prepared by dispersing lactose and biotin into water and then adding ammonia thereto.

When desired, the aqueous solution may contain any additive such as a carrier (e.g. glucose, fructose, sucrose), a preservative (e.g. sorbic acid, p-hydroxybenzoic esters) or a pigment in addition to the said essential components.

The thus prepared aqueous solution is subjected to spray-drying. The spray-drying may be carried out by a conventional procedure. As the results, there are obtained dried particles, of which each particle comprises lactose and biotin uniformly dispersed therein.

The dried particles are usually spherical and have a good flowing property. Accordingly, they can be as such evenly and easily mixed into feed supplements. Since the dried particles are low in hygroscopicity, blocks are hardly formed even in atmosphere. It is particularly characteristic that the dried particles are highly soluble in water. Therefore, they can be given to domestic animals by dissolving in drinking water or liquid feed supplements. This is quite convenient on the practical use of biotin.

Practical and presently preferred embodiments of the invention are illustratively shown in the following Examples.

EXAMPLE 1

Biotin (10 g) and lactose (490 g) were added to water (2000 ml) containing 28% aqueous ammonia in a concentration of 0.25% (w/v), followed by heating at a temperature of 60° to 70° C. The resulting solution was spray-dried by the aid of a spray drier under the following conditions to give spherical particles of 5 to 40 microns in particle size: chamber temperature, 130° to 140° C.; chamber vacuum, 30 mmH$_2$O; atomizing pressure, 2.5 kg/cm$^2$.

The thus obtained particles have a good flowing property and a critical specific humidity of 92%. Thus, they are low in hygroscopicity.

COMPARATIVE EXAMPLE 1

Biotin (10 g) and lactose (490 g) were mixed together by the aid of a V-shaped blender for 30 minutes to give a biotin preparation containing biotin in a concentration of 2% (w/w).

COMPARATIVE EXAMPLE 2

Biotin (10 g) was added to water (2000 ml) containing 28% aqueous ammonia in a concentration of 0.25% (w/v), followed by heating at a temperature of 60° to 70° C. The resulting solution was spray-dried in the same manner as in Example 1 to give particles.

COMPARATIVE EXAMPLE 3

Biotin (10 g) and lactose (490 g) were added to water (2000 ml), followed by heating at a temperature of 60° to 70° C. while stirring. The resulting dispersion was spray-dried in the same manner as in Example 1 to give particles.

The products in Example 1 and Comparative Examples 1 to 3 were each dissolved in water at room temperature, and the water-solubility of biotin in each product was determined by quantitative measurement of biotin according to the high speed liquid chromatography. The results are shown in Table 1.

TABLE 1

| Product | Amount of biotin (mg) dissolved in 100 ml of water |
|---|---|
| Example 1 | 400 |
| Comparative Example 1 | 30 |
| Comparative Example 2 | 40 |
| Comparative | 30 |

TABLE 1-continued

| Product | Amount of biotin (mg) dissolved in 100 ml of water |
|---|---|
| Example 3 | 5 |

From the above results, it is understood that the spray-drying of an aqueous solution comprising biotin and lactose with ammonia is quite effective in increasing the water-solubility of biotin.

EXAMPLE 2

Biotin (10 g) was added to water (2000 ml) containing 28% aqueous ammonia in a concentration of 0.5% (w/v), and lactose (490 g) was added thereto, followed by heating at a temperature of 60° to 70° C. The resulting solution was spray-dried in the same manner as in Example 1 to give spherical particles of 5 to 40 microns in particle size.

The thus obtained particles have a critical specific humidity of 91%. Thus, they are low in hygroscopicity. Further, the amount of biotin in them dissolved in 100 ml of water at room temperature was 400 mg.

EXAMPLE 3

Biotin (10 g) and lactose (990 g) were added to water (10 liters) containing 28% aqueous ammonia in a concentration of 0.1% (w/v), followed by heating at a temperature of 60° to 70° C. The resulting solution was spray-dried in the same manner as in Example 1 to give spherical particles of 5 to 40 microns in particle size.

The thus obtained particles have a critical specific humidity of 94%. Thus, they are low in hygroscopicity. Further, the amount of biotin in them dissolved in 100 ml of water at room temperature was 200 mg.

EXAMPLE 4

Biotin (10 g) and lactose (490 g) were mixed together and dispersed in water (2000 ml). Then, 28% aqueous ammonia (10 ml) was added thereto, followed by heating at a temperature of 60° to 70° C. The resulting solution was spray-dried in the same manner as in Example 1 to give spherical particles of 5 to 40 microns in particle size.

The thus obtained particles have a critical specific humidity of 92%. Thus, they are low in hygroscopicity. Further, the amount of biotin in them dissolved in 100 ml of water at room temperature was 350 mg.

EXAMPLE 5

Biotin (10 g), glucose (50 g), sorbic acid (1 g) and lactose (939 g) were added to water (10 liters) containing 28% aqueous ammonia in a concentration of 0.15% (w/v), followed by heating at a temperature of 60° to 70° C. The resulting solution was spray-dried in the same manner as in Example 1 to give spherical particles of 5 to 40 microns in particle size.

The thus obtained particles have a critical specific humidity of 88%. Thus, they are low in hygroscopicity. Further, the amount of biotin in them dissolved in 100 ml of water at room temperature was 260 mg.

What is claimed is:

1. A process for preparing a water-soluble biotin-containing preparation which comprises spray-drying an aqueous solution comprising biotin, lactose and ammonia to obtain dried particles containing biotin, wherein the weight proportion of biotin and lactose is from 1:40 to 1:100 and the amount of ammonia which is utilized is at least sufficient to dissolve the biotin in the solution.

2. The process according to claim 1, wherein the aqueous solution has a pH of 5 to 9.

3. The process according to claim 1, wherein the aqueous solution further comprises a member selected from the group consisting of glucose, fructose, sucrose, sorbic acid a p-hydroxybenzoic ester and a mixture thereof.

4. A water-soluble biotin-containing preparation in dried particles prepared by the process according to claim 1, which is usable as an additive to feed supplements.

* * * * *